US008465734B2

(12) United States Patent
Li et al.

(10) Patent No.: US 8,465,734 B2
(45) **Date of Patent: *Jun. 18, 2013**

(54) METHODS FOR INCREASING PROTEIN POLYETHYLENE GLYCOL (PEG) CONJUGATION

(75) Inventors: Shukuan Li, San Diego, CA (US); Zhijian Yang, San Diego, CA (US); Xinghua Sun, San Diego, CA (US); Yuying Tan, San Diego, CA (US); Shigeo Yagi, San Diego, CA (US)

(73) Assignee: AntiCancer, Inc., San Diego, CA (US)

( * ) Notice: Subject to any disclaimer, the term of this patent is extended or adjusted under 35 U.S.C. 154(b) by 192 days.

This patent is subject to a terminal disclaimer.

(21) Appl. No.: 12/875,377

(22) Filed: Sep. 3, 2010

(65) Prior Publication Data

US 2010/0331529 A1 Dec. 30, 2010

Related U.S. Application Data

(63) Continuation of application No. 12/001,304, filed on Dec. 10, 2007, now Pat. No. 7,799,549, which is a continuation of application No. 11/077,897, filed on Mar. 11, 2005, now Pat. No. 7,329,516.

(60) Provisional application No. 60/554,310, filed on Mar. 17, 2004.

(51) Int. Cl.
*A61K 38/43* (2006.01)
*C07K 17/08* (2006.01)
*C12N 9/96* (2006.01)
*G01N 33/574* (2006.01)

(52) U.S. Cl.
USPC ......... 424/94.3; 435/188; 435/7.23; 530/350; 530/402; 514/2

(58) Field of Classification Search
None
See application file for complete search history.

(56) References Cited

U.S. PATENT DOCUMENTS 5,646,113 A 7/1997 Attie et al.
5,932,462 A * 8/1999 Harris et al. .................. 435/188
5,951,974 A 9/1999 Gilbert et al.
5,985,263 A 11/1999 Lee et al.
7,329,516 B2 * 2/2008 Li et al. ......................... 435/188
7,541,328 B2 6/2009 Hemberger et al.
7,799,549 B2 * 9/2010 Li et al. ......................... 435/188

FOREIGN PATENT DOCUMENTS

JP 2000-226334 8/2000
JP 2001-526238 12/2001
WO WO-03/074087 9/2003

OTHER PUBLICATIONS

Li, 2004, Proc. Amer. Assoc. Cancer Res., 45, Abstract # 1027.*
Hoffman, 2003, Advances in Experimental Medicine and Biology, 519:69-79.*
Henmanson, Bioconjugate Techniques, Academic Press, New York, 1996, 605-629.*
Li, 2004, Proc. Amer. Assoc. Cancer Res., 45, Abstract # 1027 (vol. 45 dated Mar. 1, 2004).*
Li et al., Proc. Amer. Assoc. Cancer Res. (2004) 45:Chemistry 1, Abstract 1027.
Notice of Reasons for Rejection (translation) for JP 2007-503980, mailed Jan. 4, 2011, 5 pages.
Aguayo et al., Cancer (1999) 86:1203-1209.
Felix et al., International Journal of Peptide and Protein Research (1995) 46:253-264.
Henmanson, Bioconjugate Techniques, Academic Press (1996) New York, pp. 605-629.
Hershfield, Clin. Immunol. Immunopathol. (1995) 76:S228-S232.
Hoffman, Advances in Experimental Medicine and Biology (2003) 519:69-79.
International Search Report for PCT/US2005/008267, mailed on Aug. 8, 2006, 4 pages.
Kozlowski et al., J. Controlled Release (2001) 72:217-224.
Kuijpers et al., Journal of Biomaterials Science (2000) 11(3):225-243.
Li et al., Analytical Biochemistry (2003) 313:335-337.
Li et al., Analytical Biochemistry (2004) 330:264-271.
Masami Kimura et al., Proceedings of the Society for Experimental Biology & Medicine (1988) 188:364-369.
Pool, Science (1990) 248:305.
Sun et al., Cancer Research (2003) 63:8377-8383.
Tan et al., Protein Expression and Purification (1998) 12:45-52.
Veronese, Biomaterials (2001) 22(5):405-417.
Yamaoka et al., J. Pharm. Sci. (1994) 83:601-606.
Yang et al., Cancer Research (2004) 64:5775-5778.
Yang et al., Cancer Research (2004) 64:6673-6678.

* cited by examiner

*Primary Examiner* — Satyanarayana R Gudibande
(74) *Attorney, Agent, or Firm* — Morrison & Foerster LLP

(57) ABSTRACT

The present invention relates to highly conjugated proteins and methods for making such proteins. In particular, the present invention relates to methods for linking additional sites to a protein for conjugation with activated polyethylene glycol (PEG) linkers, without denaturing the protein. The invention also relates to highly conjugated proteins with decreased immunogenicity and increased circulating half-life.

12 Claims, 4 Drawing Sheets

METHODS FOR INCREASING PROTEIN POLYETHYLENE GLYCOL (PEG) CONJUGATION

CROSS-REFERENCE TO RELATED APPLICATION

This application is a continuation of U.S. application Ser. No. 12/001,304, filed on Dec. 10, 2007, now allowed, which is a continuation of U.S. application Ser. No. 11/077,897, filed Mar. 11, 2005, issued Feb. 12, 2008 as U.S. Pat. No. 7,329,516, and claims benefit under 35 U.S.C. §119(e) of provisional application 60/554,310 filed Mar. 17, 2004. The contents of each of these documents are expressly incorporated herein by reference in their entirety.

TECHNICAL FIELD

The present invention relates to the field of protein therapeutics, particularly highly conjugated proteins, and methods for making such proteins.

BACKGROUND ART

Conjugation of protein therapeutics with polyethylene glycol (PEG) has been shown to confer important therapeutic benefits including increased serum half-life and reduced antigenicity (Kozlowski, A., et al., *J. Controlled Release* (2001) 72:217-224). Each ethylene oxide unit of PEG associates with two to three water molecules, which results in the molecule behaving as if it were five to ten times as large as a protein of comparable molecular weight (Kozlowski, A., supra). The clearance rate of PEGylated proteins is inversely proportional to molecular weight (Yamaoka, T., et al., *J. Pharm. Sci.* (1994) 83:601-606). Below a molecular weight of approximately 20,000, the molecule is cleared in the urine. Higher-molecular-weight PEG proteins are cleared more slowly in the urine and the feces (Yamaoka, T., supra). PEGylated proteins have enhanced solubility, decreased antigenicity, decreased proteolysis, and reduced rates of kidney clearance as well as enhanced selective tumor targeting.

Currently, PEGylated forms of adenosine deaminase, asparaginase, α-IFN and a growth hormone antagonist have received regulatory approval. (Maeda, H., et al. (eds.), *Advances in experimental medicine and biology: polymer drugs in the clinical stage*, (2003) Vol. 519, Dordrecht, The Netherlands: Kluwer Academic/Plenum Publishers). PEG-α-IFN has been approved in two forms for treatment of hepatitis C. (Kozlowski, A., supra, and Gilbert, C. W., et al., U.S. Pat. No. 5,951,974 (1999)). Patients with refractory or recurrent acute lymphoblastic leukemia (ALL) are treated with a combination of PEG-asparaginase and methotrexate, vincristine, and prednisone (Aguayo, A., et al., *Cancer* (1999) 86:1203-1209). Studies also show that PEG-ADA considerably strengthened the immune system in patients with adenosine deaminase (ADA) deficiency, who are vulnerable to almost any type of infection due to inhibited development of the immune system. (Pool, R., *Science* (1990) 248:305; and Hershfield, M. S., *Clin. Immunol. Immunopathol.* (1995) 76:S228-S232). While PEGylated proteins exhibit desirable therapeutic properties, methods for protein conjugation with PEG are limited by the number and distribution of sites on proteins available for conjugation.

DISCLOSURE OF THE INVENTION

The present invention relates to highly conjugated proteins and methods for making such proteins. In particular, the present invention relates to methods for chemical coupling of polyalkylene oxides to therapeutic proteins, resulting in highly conjugated proteins with decreased immunogenicity and increased circulating half-life.

In one aspect, the present invention relates to methods for modifying a protein with a non-protein polymer chain, comprising: a) coupling a protein with a non-protein polymer to form a first modified protein having one or more non-protein polymer chains; b) coupling the first modified protein having one or more non-protein polymer chains with a polyfunctional amine having at least two amino groups to form a modified protein having one or more additional amino groups; and c) coupling the modified protein having one or more additional amino groups with another non-protein polymer to form a second modified protein having more non-protein polymer chains than the first-modified protein.

In one example, the non-protein polymer is derivatized with a functional group capable of reacting with an N-terminal amino group of the protein. For example, the non-protein polymer may be derivatized with N-hydroxysuccinimide. In one example, the non-protein polymer is a polyoxyalkylene such as polyethylene glycol. In a particular example, the functionalized non-protein polymer is methoxypolyethylene glycol succinimidyl glutarate. Generally, the non-protein polymer has a molecular weight of about 5000.

In step a), the first modified protein may be formed by coupling an N-terminal amino group in the protein with an ester group in the non-protein polymer. In step 2, the modified protein having one or more additional amino groups may be formed by coupling a C-terminal carboxyl group in the first modified protein with an amino group in the polyfunctional amine. The polyfunctional amine may be diaminobutane. In one example, the carboxyl is coupled to the polyfunctional amine in the presence of a catalyst, such as carbodiimide. In a particular example, the carboxyl is coupled to the polyfunctional amine in the presence of 1-ethyl-3-(3-dimethylaminopropyl)carbodiimide. In one example, the modified protein is formed in the second coupling step without crosslinking between first modified proteins.

In one example, the ratio of protein to non-protein polymer in the first coupling step is 1:15. In another example, the ratio of first modified protein to non-protein polymer in the second coupling step is 1:60.

The present invention also provides proteins modified according to the methods described above. In one example, the protein is highly conjugated methioninase. Furthermore, the present invention provides a protein that is twice modified with polyethylene glycol chains, wherein the first modification comprises coupling the N-terminal amino group of a protein with a polyethylene glycol ester derivative to form an initially PEGylated protein, and coupling the C-terminal carboxyl group of the initially PEGylated protein with a polyfunctional amine having at least two amino groups to form a first modified protein having polyethylene glycol chains and one or more additional amino groups; and wherein the second modification comprises coupling one or more additional amino groups in the second modified protein with another polyethylene glycol ester derivative to form a second modified protein with more polyethylene glycol chains than the first modified protein. The present invention also provides pharmaceutical compositions, comprising the modified proteins of the present invention, and a pharmaceutically acceptable excipient.

Furthermore, the present invention provides methods for modulating tumor activity, comprising administering to a subject in need thereof a therapeutically effective amount of the modified proteins of the present invention, or a pharmaceutical composition thereof. The subject may be human or animal.

As used herein, the term "polyfunctional amine" refers to an amine having at least one functional amino group. In one example, aliphatic polyfunctional amines, preferably diamines, are used as coupling agents. Aliphatic polyfunctional amines having three or more functional amino groups, as well as aromatic polyfunctional amines are also contemplated for use as coupling agents. Examples of aliphatic polyfunctional amines include but are not limited to 1,4-diaminobutane, 1,2-diamino-2-methylpropane, 1,5-diaminopentane, 2,2-dimethyl-1,3-propanediamine, 1,6-hexanediamine, diethylenetriamine and triethylenetetraamine. In one example, 1,4-diaminobutane is used as a coupling reagent. Examples of aromatic polyfunctional amines include but are not limited to p-phenylenediamine, p-toluoylenediamine and diaminonaphthalane.

As used herein, the term "coupling agent" refers to any substance capable of forming a bonding link between two reagents. In one example, a carbodiimide is used to couple an amino and a carbonyl group such as an ester or an acid. Examples of carbodiimides include but are not limited to 1-ethyl-3-(3-dimethylaminopropyl)carbodiimide, dicyclohexyl carbodiimide, diisopropyl carbodiimide, bis(trimethylsilyl)carbodiimide, or N-cyclohexyl-N'-(β-[N-methylmorpholino]ethyl)carbodiimide p-toluenesulfonate. In one example, 1-ethyl-3-(3-dimethylaminopropyl)carbodiimide is used to couple an N-terminal amino group on a protein to a carbonyl group such as an ester or an acid.

As used herein, the terms "activated polyethylene glycol" or "activated PEG" refer to a polyethylene glycol which has been derivatized with a more reactive functional group. In a particular example, the activated polyethylene glycol has been derivatized with a functional group capable of reacting with lysine or N-terminal amino groups of proteins. Methods of activating polyethylene glycol are well-known to those skilled in the art. For example, polyethylene glycol may be esterified to N-hydroxysuccinimide to form an activated PEG ester.

MODES OF CARRYING OUT THE INVENTION

Figure 1:
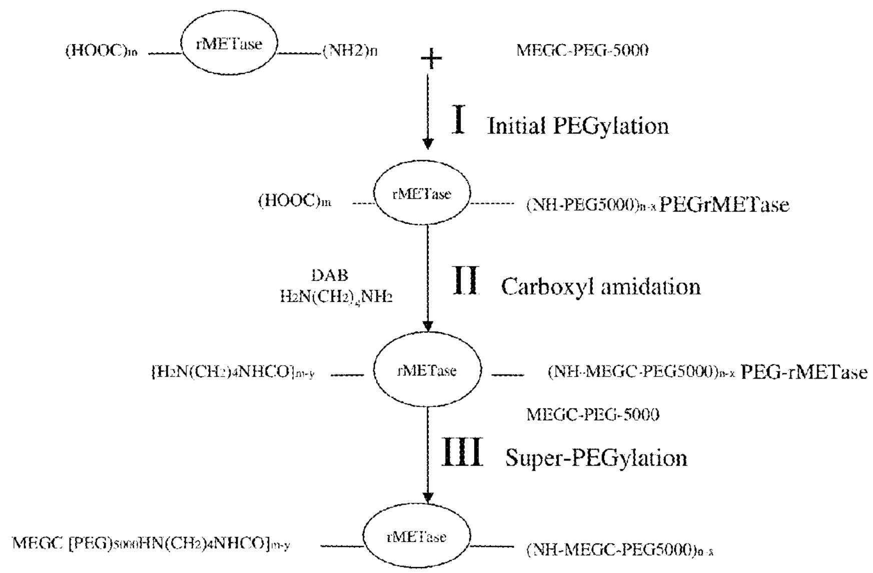
FIG. 1 describes a scheme for preparing super-PEG-rMETase.

The present invention relates to highly conjugated proteins and methods for making such proteins. In particular, the present invention relates to methods for linking additional sites to a protein for conjugation with activated polyethylene glycol (PEG) linkers, without denaturing the protein. The invention also relates to highly conjugated proteins with decreased immunogenicity and increased circulating half-life.

To couple PEG to a protein, the polymer is first activated by converting the hydroxyl terminus to a functional group capable of reacting typically with lysine and N-terminal amino groups of proteins (Kozlowski, A., supra). As PEG modification is based on the reaction between the ε amino group of lysine residues in a protein and activated esters of PEG, the effect of PEG modification for any protein mainly depends on the numbers and distribution of PEG attachment sites (Hershfield, M. S., et al., *Proc. Natl. Acad. Sci. USA* (1991) 88:7185-7189). One option to increase available sites for PEGylation is site-directed mutagenesis, which replaces specific amino acid in the protein with lysine (Hershfield, M. S., supra; and He, X. H., et al., *Life Sci*. (1999) 65:355-368). Alternatively, chemical coupling methods may be used. (Davis, F. F., et al., U.S. Pat. No. 4,179,337 (1979); Veronese, F. M., *Biomaterials* (2001) 22:405-417; and Kimura, M., et al., *Proc. Soc. Exp. Biol. Med*. (1988) 188:364-369).

Chemical coupling methods for adding PEGylation sites in a protein is based on a water-soluble carbodiimide-mediated reaction that enables carboxyl groups in proteins to react with additional amino groups of a polyfunctional amine. This method therefore adds reactive amino groups suitable for PEGylation to carboxyl groups in a protein. However, this approach has been limited by cross-linking reactions resulting in polymeric forms of carboxyl-amidated proteins or peptides (Davis, F. F., supra).

The methods of the present invention provide additional linking sites to a protein for conjugation with activated polyethylene glycol (PEG) linkers, without denaturing the protein. (Li et al., *Anal. Biochem.* 330:264-271 (2004), hereby incorporated by reference). The highly conjugated proteins have been shown to exhibit a decreased immunogenicity and an extended half-life. (Yang et al., *Cancer Res.* 64:6673-6678 (2004), hereby incorporated by reference). The circulating half-life of a highly conjugated protein has also been shown to be highly dose dependent on cofactor pyridoxal-5'-phosphate. (Yang et al., *Cancer Res.* 64:5775-5778 (2004), hereby incorporated by reference).

Generally, the method comprises: a) coupling a protein with a non-protein polymer to form a first modified protein having one or more non-protein polymer chains; b) coupling the first modified protein having one or more non-protein polymer chains with a polyfunctional amine having at least two amino groups to form a modified protein having one or more additional amino groups; and c) coupling the modified protein having one or more additional amino groups with another non-protein polymer to form a second modified protein having more non-protein polymer chains than the first-modified protein.

The methods of the present invention are illustrated in a model recombinant protein, L-methionine-α-deamino-γ-mercaptomethane lyase (rMETase). However, the methods of the present invention are not limited to conjugation of rMETase, and are generally applicable to other proteins. rMETase has only 9 lysine residues out of 398 amino acids per monomer, far lower than the normal frequency of this amino acid occurring in most proteins. In contrast, there are 37 carboxyl groups in each subunit of rMETase to couple additional amino groups for PEGylation.

L-methionine α-deamino-γ-mercaptomethane lyase (METase) [EC 4.4.1.11] from *Pseudomonas putida* has been previously cloned and produced in *Escherichia coli* (Tan Y., et al., *Protein Expr. Purif.* (1997) 9:233-245; Inoue, H., et al., *J. Biochem*. (1995) 117:1120-1125; and Hori, H., et al., *Cancer*

*Res*. (1996) 56:2116-2122). Recombinant methioninase (rMETase) is an enzyme active in preclinical mouse models of human cancer. The efficacy of rMETase is due to depletion of plasma methionine, an amino acid for which tumors generally have an abnormally high methionine requirement. Furthermore, transient methionine depletion results in a markedly increased sensitivity of the tumors to several chemotherapeutic agents (Tan, Y., et al., *Clin. Cancer Res*. (1999) 5:2157-2163; Yoshioka, T., et al., *Cancer Res*. (1998) 2583-2587; and Kokkinakis, D. M., et al., *Cancer Res*. (2001) 61:4017-4023).

rMETase has been previously coupled to methoxypolyethylene glycol succinimidyl glutarate-5000 (MEGC-PEG-5000) to prolong its circulating half-life, and thus extend the in vivo period of depletion of plasma and tumor methionine. One sub-unit of rMETase was modified by approximately 4, 6 and 8 PEG molecules when rMETase was PEGylated at molar ratios of PEG/rMETase of 30/1, 60/1, and 120/1, respectively. PEG-rMETase (120/1) had a serum half-life increase of 20-fold, and methionine depletion time increased 12-fold compared to unmodified rMETase. The increase in in vivo half-life depended on the extent of PEGylation of rMETase. PEGylation also reduced the immunogenicity of rMETase. The extent of reduction in immunogenicity depended on the number of residues PEGylated (Sun, X., et al., *Cancer Research* (2003) 63:8377-8383).

FIG. 1 shows a three-step preparation of super-PEGylated rMETase without cross-linking of rMETase molecules, involving initial PEGylation, carboxyl amidation, and super-PEGylation. First, rMETase is initially PEGylated with methoxypolyethylene glycol succinimidyl glutarate (MEGC-PEG-5000). In particular embodiments, initial PEGylation is carried out using a 15:1 ratio of PEG to rMETase.

Second, carboxyl groups of the initially-PEGylated protein is subsequently conjugated with a polyfunctional amine such as diaminobutane (DAB), resulting in carboxyl amidation. In particular embodiments, carboxyl amidation is carried out in the presence of a catalyst such as a water soluble carbodiimide. Although the present invention is not limited by the mechanism of conjugation, cross-linking between rMETase molecules during carboxyl amidation may be inhibited by the steric hindrance provided by the PEG chains already coupled to the protein.

Third, the carboxyl-amidated PEGylated rMETase was super-PEGylated by further coupling the amino group in the carboxyl-amidated PEGylated rMETase with methoxypolyethylene glycol succinimidyl glutarate. In particular embodiments, super-PEGylation was carried out at a ratio of PEG to PEG-rMETase of 60:1. Biochemical analysis indicated that 13 PEG chains were coupled to each subunit of rMETase after super-PEGylation compared with 6~8 PEG chains attached to the non-carboxyl-amidated PEG-rMETase. Approximately 15-20% of the non-PEGylated rMETase activity was retained in the super-PEGylated molecule. Immunogenicity of the super-PEG-rMETase was significantly reduced relative to PEG-rMETase and rMETase. Initial results suggest super-PEGylation may become a new strategy for PEGylation of protein biologics.

Table 1 shows the effect of each step of the reaction on the specific activity of rMETase. In Table 1, the starting material was 200 mg of rMETase, with a specific activity of 56 U/mg. Recovery is calculated based on comparing specific activity of naked rMETase with each modified rMETase. As shown in Table 1, the carboxyl amidation reaction caused the greatest loss of specific activity.

TABLE 1

Protein and activity recovery of rMETase during carboxyl-amidation-mediated super-PEGylation of rMETase

| Steps | Total Volume (ml) | Total activity (U) | Total protein (mg) | Specific activity (U/mg) | Recovery % |
|---|---|---|---|---|---|
| Step I Initial PEGylation | 8 | 9280 | 200 | 46.4 | 82.8 |
| Step II Carboxyl amidation | 2 | 2538 | 152 | 16.7 | 29.8 |
| Step III Super-PEGylation | 5.1 | 884.8 | 112 | 7.9 | 14.1 |

Effect of Different Reaction Conditions on the Carboxyl Amidation of rMETase

Figure 2:
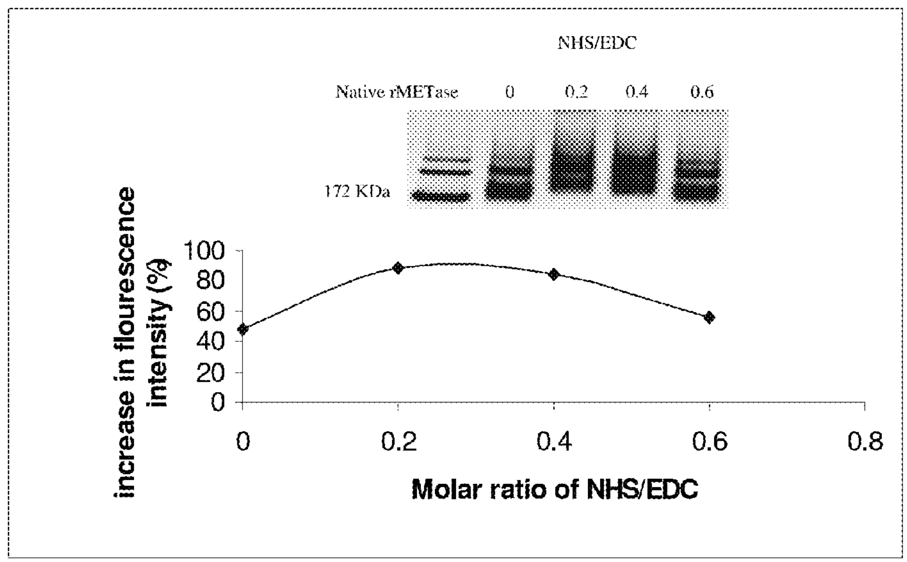
FIG. 2 shows the effect of the molar ratio of NHS/EDC on the extent of carboxyl amidation of rMETase.

FIG. 2 shows the effect of the molar ratio of N-hydroxysuccinimide to 1-ethyl-3-(3-dimethylaminopropyl) carbodiimide (NHS/EDC) on the degree of carboxy amidation of rMETase. Carboxyl amidation of rMETase was carried out with different NHS/EDC ratios. The extent of carboxyl amidation was evaluated by fluorescamine method and native PAGE. Fluorescence intensity with excitation at 475 nm and emission at 475 nm indicate the number of free amino groups in the protein. Gels (inset) indicated MW increase of rMETase due to carboxyl amidation. Ratios of rMETase/diaminobutane (DAB) and rMETase/EDC of 1:600 and 1:800, respectively, were used. The difference in fluorescence intensity and electrophoresis mobility of the carboxyl amidated rMETases were compared with rMETase.

An NHS/EDC ratio of 0.2 enabled the highest extent of coupling DAB to rMETase. Smaller or larger DAB ratios decreased the degree of coupling. NHS enhanced the carboxyl amidation reaction mediated by EDC. However, the optimal efficiency of this enhancement depended on an optimal ratio of NHS/EDC. The results from this study were similar to the results obtained by other investigators (Kuijpers, A. J., et al., *J. Biomater. Sci. Polym*. (2000) 11:225-243).

Figure 3:
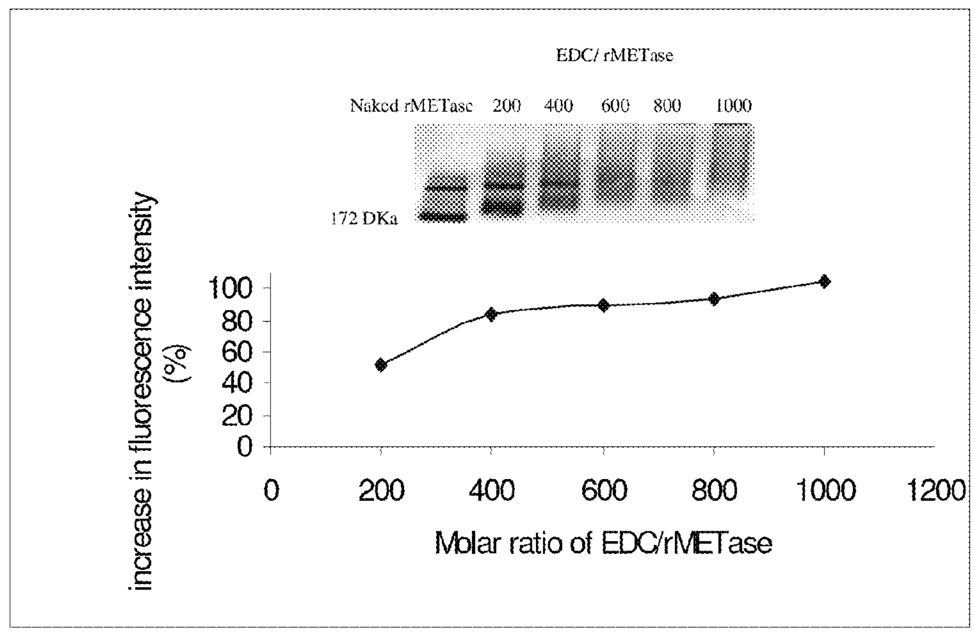
FIG. 3 shows the effect of the molar ratio of EDC/rMETase on the extent of carboxyl amidation of rMETase.

The effect of the ratio of EDC/rMETase on the carboxyl amidation reaction was determined by fixing the concentration of DAB at 9.4 mg/ml and keeping NHS/EDC at a ratio of 0.2. The results demonstrate that the degree of rMETase coupled by DAB was dependent on the ratio of EDC/rMETase (FIG. 3). Carboxyl amidation of rMETase was carried out with varying molar ratios of EDC/rMETase. The carboxyl amidated r-METases were analyzed using the fluorescamine method and native PAGE (see FIG. 2). Ratios of NHS/EDC at 0.2, and rMETase/DAB at 1:600 were used. The differences in fluorescence intensity and electrophoresis mobility of the carboxyl amidated rMETases were compared with rMETase. The higher the ratio of EDC/rMETase, the higher the extent of carboxy amidation of rMETase. In particular embodiments, the molar ratio of EDC/rMETase does not exceed 800.

Figure 4:
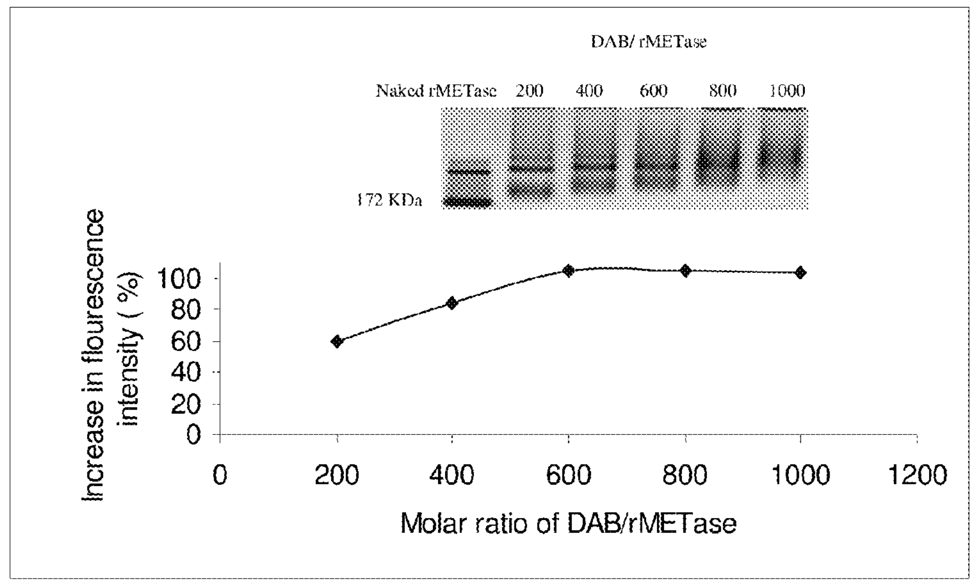
FIG. 4 shows the effect of the molar ratio of diaminobutane (DAB)/rMETase on the extent of carboxyl amidation of rMETase.

FIG. 4 shows the effect of DAB/rMETase on the extent of carboxyl amidation. Carboxyl amidation of rMETase was carried out with varying molar ratios of EDC/rMETase. Molar ratios of NHS/EDC and rMETase/EDC at 0.2 and 1:800, respectively, were used. Carboxyl amidated rMETases were analyzed with the fluorescamine method and native PAGE and compared with rMETase. When the ratio of DAB/rMETase increased to 600, the extent of carboxyl amidation appeared to reach a plateau. In particular embodiments, the ratio of DAB/rMETase in the carboxyl amidation reaction does not exceed 600.

Figure 5:
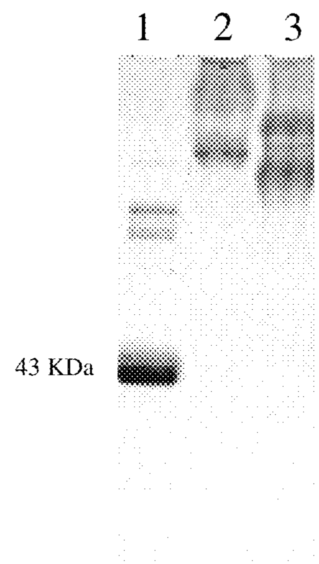
FIG. 5 shows an SDS-PAGE of rMETase and PEGylated rMETases.

The EDC-mediated carboxyl amidation of rMETase was completed within 30 minutes. This reaction enabled production of super PEG-rMETase with a PEG:carboxyl amidated PEG-rMETase of 60:1 (FIG. 5). Therefore, in certain embodiments, it is unnecessary to maintain a protein in the reaction system for a long time as previously reported (Kimura, M., supra). Rather, a short incubation time may be used to reduce the loss of rMETase activity caused by harsh reaction conditions.

Characterization of Super-PEGylated PEG-rMETase

Native rMETase, PEG-rMETase, and super-PEGylated rMETase were analyzed on 10% SDS-polyacrylamide gel. FIG. 5 shows that the new super-PEGylated rMETase had the lowest mobility and highest molecular weight. In FIG. 5, lanes 1, 2 and 3 relate to native rMETase, Super PEG-rMETase and PEG-rMETase, respectively. The 10% SS gels were stained with Coomassie brilliant blue. These data suggest that super-PEGylated PEG-rMETase was conjugated to a greater number of PEG chains than PEG-rMETase.

Using a colorimetric assay (Li, S., et al., *Anal. Biochem.* (2003) 313:335-337), the free and coupled PEG content in the final products of PEG-rMETase and super-PEG-rMETase were quantified. Approximately 13 PEG chains were coupled to each subunit of super-PEG-rMETase (Table 2) compared to approximately 7 PEG chains coupled to PEG-rMETase. These results suggest that additional amino groups had been introduced by carboxy amidation.

As a control, rMETase was PEGylated in two steps without an intervening carboxyl amidation step. Super-PEG-rMETase was prepared by initial PEGylation at PEG: rMETase of 15:1, followed by carboxyl amidation and then super-PEGylation at PEG:rMETase of 60:1. As shown in Table 2, this resulted in only 6 PEG's per rMETase subunit, demonstrating the effect of carboxyl amidation on super-PEGylation of rMETase.

TABLE 2

Effect of protein carboxyl amidation on extent of rMETase PEGylation

| PEGylated rMETase | Coupled PEG's rMETase (mg/mg) | Degree of modification (mol PEG/mol rMETase subunit) |
|---|---|---|
| PEG-rMETase with no carboxyl amidation | 0.82 | 6.9 |
| Super-PEG-rMETase with carboxyl amidation | 1.54 | 13.2 |

Figure 6:
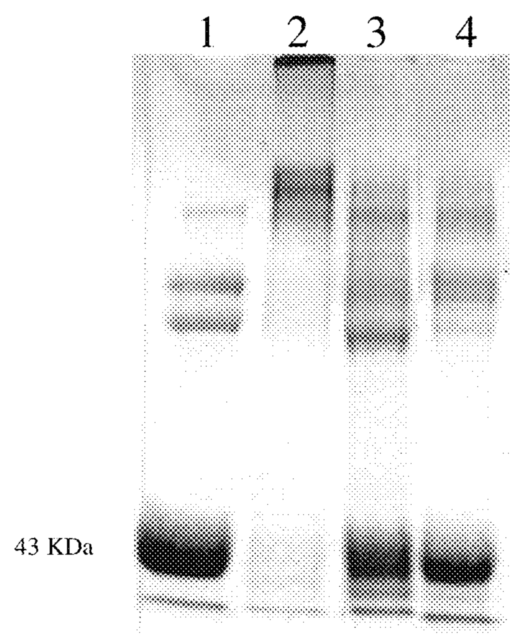
FIG. 6 shows the effect of cross-linking on initial PEGylation during carboxyl amidation of rMETase.

Effect of Initial PEGylation on Reducing Cross-Linking of rMETase in the Carboxyl Amidation Reaction When unmodified rMETase was directly reacted with DAB without initial PEGylation, rMETase precipitated in the reaction solution apparently due to the cross linking, leading to the significant loss of rMETase activity. Therefore, a major limit to adding amino groups to proteins using carboxyl amidation is cross linking of the reacting protein. Initial PEGylation greatly reduced cross-linking during the carboxyl amidation reaction. With initial PEGylation, there was no difference in molecular weight between PEG-rMETase and super-PEG-rMETase after alkaline hydrolysis to remove all PEG chains (FIG. 6). Native rMETase and of PEG-rMETases were subjected to alkaline hydrolysis and analyzed on 10% SDS-polyacrylamide gels.

In FIG. 6, lanes 1-4 correspond to the following: 1) native rMETase; 2) super PEG-rMETase after carboxyl amidation of unPEGylated rMETase; 3) super PEG-rMETase prepared in the 3-step process with initial PEGylation, carboxyl amidation, and super-PEGylation; and 4) control PEG-rMETase. All the samples tested, including native rMETase, were 4 mg/ml in 100 μl distilled water. Two μl of sodium hydroxide (10N) was added to each sample. After 30 min, 1.8 μg of HCl (10N) was added to stop the alkaline hydrolysis reaction. Approximately 12 μg rMETase was loaded to each well of the gels.

These data indicated no detectable cross linking had occurred during the carboxyl amidation reaction. In contrast, super-PEG-rMETase conjugate not initially PEGylated before carboxyl amidation resulted in a significant amount of cross-linking, as shown after alkaline hydrolyses and SDS PAGE with the cross-linked rMETase remaining at the top of the gel (FIG. 6, lane 2). Although the mechanism of prevention by initial PEGylation of cross-linking during carboxyl amidation is not necessary to practice the methods of the invention, the activated PEG is believed to react with the most easily accessible amino groups on the rMETase molecular surface, markedly reducing their chance of reacting with carboxyl groups of other rMETase molecules. In addition, the PEG chains have a very large exclusion volume (Knoll, D., et al., *J. Biol. Chem.* (1983) 258:5710-5715) thereby inhibiting other macromolecules from reacting with the initially PEGylated rMETase. Therefore, PEG chains attached to rMETase in the initial PEGylation process may prevent cross-linking during subsequent carboxyl amidation.

Comparison of Immuno Reactivity of rMETase, PEG-rMETase, and Super-PEG-rMETase

One of the most important features of PEGylation is the reduction of antigenicity and immunogenicity of PEGylated proteins. The extent of antigen-antibody (Ag-Ab) recognition is an important gauge of immunogenicity of a protein. The immunoreactivity of naked rMETase, PEG-rMETase, and super-PEG-rMETase was therefore evaluated by their binding capacity with mouse anti-rMETase serum.

Figure 7:
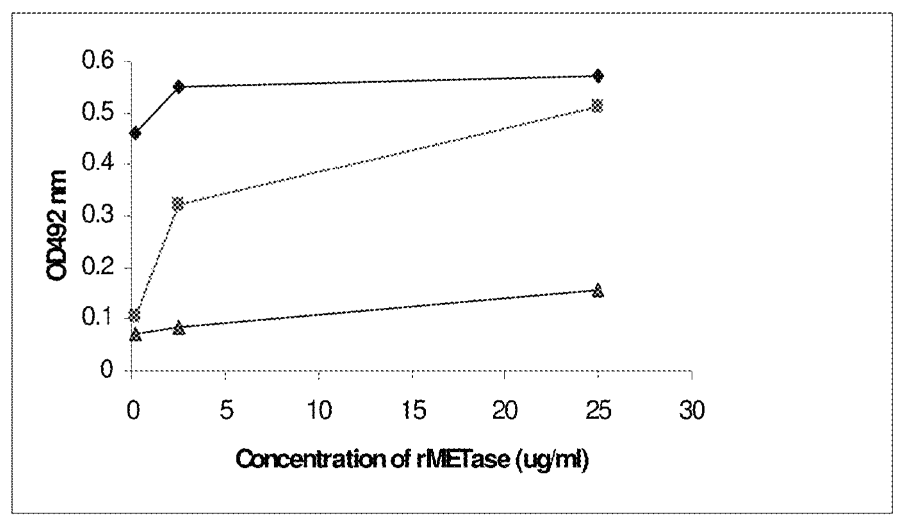
FIG. 7 compares the immunoreactivity of native rMETase (♦), PEG-rMETase (■), and super PEG-rMETase (▲).

FIG. 7 shows the antibody binding capacity of native rMETase and the two types of PEGylated rMETase as a function of their concentration. The immunoreactivity assay was performed by ELISA in the sandwich format. Rabbit anti-rMETase antiserum was used for coating the microplates. Native rMETase, PEG-rMETase, and super-PEG-rMETase were captured and then reacted with mouse anti-rMETase antiserum. The coupled mouse anti-rMETase antiserum was detected by using goat antimouse polyvalent immunoglobulins conjugated with horseradish peroxidase. The absorbance values at $OD_{492}$ nm determined the binding of native or PEG-rMETase with anti-rMETases antibody. Results were compared at three dilution levels. (♦) Native rMETase; (■) PEG-rMETase; (▲) Super PEG-rMETase.

The data indicate the binding capacity of PEG-rMETase to anti-rMETase was reduced to some extent. The binding ability of super PEG-rMETase with anti-rMETase serum was significantly lower than regular PEG-rMETase. The results suggest that the super-PEG-rMETase had reduced antigenicity. The significant reduction in antigenicity confirmed the effectiveness of increasing PEGylation of rMETase through carboxyl amidation. Future experiments will determine the in vivo efficacy of super-PEG-rMETase.

EXAMPLES

The following examples are offered to illustrate but not to limit the invention. In the following examples, recombinant methioninase (rMETase) was produced by fermentation of *E. coli* (Tan, Y., supra). Sephacryl S-300, Sephadex G-25 was purchased from Amersham Pharmacia Biotech (Piscataway, N.J.). Pre-cast Tris-Glycine gels were from NOVEX (San Diego, Calif.). Rabbit antiserum against rMETase was obtained from H.T.I Bio-Products, Inc., San Diego, Calif. Goat anti-mouse polyvalent immunoglobulins and horseradish peroxidase conjugate were purchased from Sigma (St. Louis, Mo.). Fluorescamine, 1-ethyl-3-(3-dimethylaminopropyl) carbodiimide (EDC), 1,4-diaminobutane (DAB) dihydrochloride, N-hydroxysuccinmide, and ammonium thiocyante were purchased from Fisher Scientific (Fairlawn, N.J.). Monomethoxy polyethylene glycol succinimidyl glutarate-5000 (MEGC-5000) PEG was a gift from the NOF corporation (Tokyo, Japan).

Example 1

Fluorescamine Method to Estimate the Extent of Carboxyl Amidation Groups in rMETase The fluorescamine method is usually used to estimate the degree of PEGylation, based on the reduction in fluorescence intensity due to conjugation of amino groups by activated PEG's. Here, the fluorescamine method was used to estimate the extent of carboxyl amidation of rMETase by detecting the increase in fluorescence intensity after rMETase was coupled with diaminobutane (DAB). The assay procedure basically followed the method described by Stocks (Stocks, S. J., et al., *Anal. Biochem.* (1986) 154:232-234). Briefly, various amounts of rMETase and PEGylated rMETase in 2 ml of 0.1 M sodium phosphate buffer, pH 8.0 were mixed with 1 ml fluorescamine solution (0.3 mg/ml in acetone) and kept for 5 min at room temperature. Samples were then assayed with a fluorescence spectrophotometer at 390 nm excitation and 475 nm emission. Results were plotted as fluorescence intensity versus the concentrations of rMETase, with the slope of the line being determined by linear regression.

The increased fluorescence intensity percentage (%) was presented as: [(slope of fluorescence intensity after coupling with DAB—slope of fluorescence intensity of naked rMETase)/slope of fluorescence intensity of naked rMETase]×100.

Determination of Protein Content

The protein concentration of native rMETase was measured with the Wako Protein Assay Kit (Wako Pure Chemical, Osaka, Japan) according to the instruction manual. Bovine serum albumin (BSA) was used as the standard. The protein content of the PEG-rMETase conjugate was determined by ultraviolet (UV) absorbance at 280 nm Naked rMETase was used to make the standard curve.

Polyacrylamide Gel Electrophoresis (PAGE)

All electrophoresis experiments were carried out with an Xcell II system using 10% NOVX pre-cast gels according to the instruction manual. For performing SDS-PAGE, tris-glycine running buffer containing SDS was used. The proteins in the gel were stained with Coomassie brilliant blue. All modified rMETases were compared with naked rMETase.

Example 2

Reaction Conditions for Carboxy Amidation of r-METase

A. Optimizing the N-hydroxysuccinimide (NHS) 1-ethyl-3-(3-dimethylaminopropyl) carbodiimide (EDC) ratio.

Keeping the molar ratio of rMETase/DAB and rMETase/EDC at 1:600 and 1:800, respectively, the optimal molar ratio of NHS/EDC was determined. DAB (14.1 mg), along with varying amounts of NHS, 4.0 mg, 2.7 mg, 1.3 mg, and 0 mg, respectively, (corresponding to NHS/EDC ratios of 0.6, 0.4, 0.2, 0, respectively) were dissolved in distilled water. The pH of each solution was adjusted to 6.5 with 0.5 N NaOH, to obtain a final volume of 1 ml. These solutions were transferred into 4 wells of a tissue culture plate. Then 25 mg of rMETase in 0.5 ml of 0.2 M sodium phosphate buffer (pH 6.5) was added to each well. The carboxyl amidation reaction was started by addition of 22.2 mg EDC. After stirring for 4 h at room temperature, the products were applied on a Sephadex G-25 column previously equilibrated with 0.1 M, pH 7.4 PBS to remove small molecular impurities. The extent of coupling rMETase with DAB was then evaluated by using PAGE and the fluorescamine method.

B. Optimizing the rMETase/EDC and rMETase/DAB Ratios

The effect of EDC on the carboxyl amidation reaction was determined using the optimal molar ratio of NHS/EDC of 0.2 determined from experiment A above and a rMETase/DAB ratio of 1:600. Varying amounts of EDC that correspond to rMETase/EDC molar ratios of 1:200, 1:400, 1:600, 1:800, and 1:1000 were added to each well which had 1.5 ml of a mixture of PBS (0.2 M, pH 6.5) containing 25 mg rMETase, 14.1 mg DAB, and 1.3 mg NHS. The other reaction conditions, processing and the evaluation methods for the final coupled products were the same as in experiment A. To obtain an optimal molar ratio of rMETase/DAB, keeping the NHS/EDC ratio at 0.2, as well as the determined optimal rMETase/EDC ratio at 1:800, the same procedures as described above were carried out.

C. Time Course of Carboxy Amidation Reaction

The time course reaction used 33 mg rMETase in 2 ml PBS (0.2 M, pH 6.5) with NHS/EDC at 0.2, rMETase/DAB at 1:800, and rMETase/EDC at 1:800. After starting the reaction by adding EDC, 0.4 ml of reactant was removed at various time intervals and then purified. The extent of rMETase coupled with DAB was analyzed as described above.

Example 3

Preparation of Super-PEGylated rMETase

Super-PEGylated rMETase with more PEG chains than that previously obtained with non-carboxyl-amidated rMETase was prepared following a three-step procedure as shown in FIG. 1. To introduce additional primary amines without cross-linking between rMETase molecules, native rMETase was first PEGylated, which subsequently enabled carboxyl amidation without cross linking. Finally, the carboxyl-amidated r-METase was "super"-PEGylated. For the initial PEGylation step, two ml (200 mg) of rMETase in PBS (0.1 M, pH 7.4) was adjusted to pH 8.5 with 0.5 N NaOH, and then reacted with 87.2 mg of MEGC-5000 PEG (molar ratio of PEG to rMETase at 15:1) with stirring for 1 hr at room temperature.

To couple DAB to the carboxyl groups of the initially PEGylated rMETase, the reactants were diluted with 4 ml of PBS (0.2 M, pH 6.5) to 8 ml of containing 21.3 mg NHS (NHS/EDC at 0.2), 149.8 mg DAB (rMETase/DAB at 1:600), 178.3 mg EDC (rMETase/EDC at 1:800). After agitation for 30 minutes, the mixture was applied on an Sephacryl S-300 column (26×60) which was eluted with PBS (0.05 M, pH 7.4) in order to remove free PEG and the other small molecular impurities. The carboxyl amidated PEG-rMETase was then super PEGylated as described below:

For super PEGylation, 152 mg of PEG-rMETase containing newly-added primary amines was concentrated to 2 ml. To start the super-PEGylation reaction, 0.2 ml borate buffer (1

M, pH 9.0) was added along with 265.1 mg MEGC-PEG-5000 (molar ratio of PEG:PEG-rMETase of 60:1) with pH adjustment to 8.5. After purification and concentration, 112 mg of super-PEG-rMETase was obtained. As a control, PEG-rMETase was also prepared in a two-step mode with PEG-rMETase 15:1 and 60:1, respectively, as above but without carboxyl amidation.

Example 4

Determination of PEGylation Extent of rMETase

The degree of rMETase PEGylation was determined as the average PEG content per rMETase subunit. The quantification of PEG content in the final purified PEG-rMETase conjugate was performed using the alkaline-hydrolysis colorimetric method described by Li, S., et al., supra. Briefly, the PEG-rMETase to be analyzed was divided into two samples. One sample was subjected to alkaline hydrolysis for 30 min to release the PEG coupled with rMETase. The other sample of PEG-rMETase was not subject to alkaline hydrolysis. Each sample were then introduced into a biphasic system consisting of one ml chloroform and one ml ammonium thiocyanate. After vigorous vortexing for 30 min and centrifugation at 3500 g for 3 min, the lower layer of chloroform was removed. Optical density at 510 nm was used to determine the amount of free or released PEG in the chloroform layer with use of a standard curve. The amount of free PEG in the PEG-rMETase preparation was determined from the sample without alkaline hydrolysis treatment. The total amount of PEG in PEG-rMETase was determined in the sample subjected to alkaline hydrolysis. The amount of PEG coupled to rMETase was obtained by the total amount of PEG minus the free amount (Li, S., supra).

Example 5

Immunoreactivity of rMETase, PEG-rMETase, and Super-PEGylated rMETase

The immunoreactivity of naked rMETase and the PEGylated rMETases was determined by their binding capacity to anti-rMETase antiserum. The immunoreactivity assay was performed using ELISA and the sandwich format. One-hundred μl of rabbit anti-rMETase antiserum diluted with 0.1 M sodium carbonate coating buffer (pH 9.5) was added to each well in the microplate and incubated at 4° C. overnight. The plate was washed three times with PBS (pH 7.4) containing 0.05% Tween-20, blocked for 2 h at room temperature with 200 μl of pH 7.4 PBS assay buffer containing 10% FBS, and washed again. One-hundred μl of rMETase, PEGylated rMETase, and super-PEGylated rMETase diluted from 25 μg/ml to 0.25 μg/ml in PBS assay buffer were added to appropriate wells of the microplate and incubated for 1 h at room temperature. After the plate was washed, 100 μl of mouse anti-rMETase antiserum was added to each well of the plate and incubated for 1 h at room temperature, followed by washing. One-hundred μl of goat anti-mouse polyvalent immunoglobulin and horseradish peroxidase conjugate with optimal dilution were added to each well. The plate was incubated for 1 h at room temperature and washed three times. One-hundred μl of substrate solution (O-phenylenediamine dihydrochloride+hydrogen peroxide) was added to each well, followed by 30 min incubation at room temperature. Fifty μl of 2 N sulfuric acid was added to each well to stop the color reaction. The absorbance of each well was measured at 492 nm.

It is understood that the foregoing detailed description and accompanying examples are merely illustrative, and are not to be taken as limitations upon the scope of the invention. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof. U.S. patents and publications referenced herein are incorporated by reference.

The invention claimed is:

1. A modified methioninase protein wherein said modification comprises at least one first polyethylene glycol (PEG) polymer coupled to at least one amino group of said methioninase and at least one second PEG polymer coupled to a carboxyl group of said methioninase through a polyamine linker, wherein one amino group of said polyamine linker forms an amide with said carboxyl group of the methioninase and at least one additional amino group is coupled to said second PEG polymer.

2. The modified methioninase of claim 1 wherein more than one first PEG polymer are coupled to more than one amino group of said methioninase.

3. The modified methioninase of claim 1 wherein more than one second PEG polymer are coupled to more than one amino group of said polyamine linker.

4. The modified methioninase of claim 2 wherein more than one second PEG polymer are coupled to more than one amino group of said polyamine linker.

5. The modified methioninase of claim 1 which comprises six to eight first PEG polymers and six second PEG polymers.

6. The modified methioninase of claim 1 which is prepared by a process which comprises coupling at least one second PEG polymer to at least one amino group of a polyamine linker that forms an amide with at least one carboxyl group of said methioninase, and wherein said methioninase comprises at least one first PEG polymer coupled to at least one amino group of said methioninase.

7. The modified methioninase of claim 6 wherein said process comprises coupling more than one second PEG polymer to more than one amino group of said polyamine linker.

8. The modified methioninase of claim 1 which is a recombinant methioninase.

9. The modified methioninase of claim 1 wherein the poly functional amine linker is diaminobutane.

10. A pharmaceutical composition comprising the modified methioninase of claim 1 and a pharmaceutically acceptable excipient.

11. A method to modulate tumor activity comprising administering to a subject in need thereof a therapeutically affected amount of the modified methioninase of claim 1 or a pharmaceutical composition thereof.

12. The method of claim 11 wherein the subject is human.

* * * * *